United States Patent [19]

Frisch et al.

[11] Patent Number: 5,753,591
[45] Date of Patent: May 19, 1998

[54] AQUEOUS SUSPENSION CONCENTRATES OF ENDOSULFAN

[75] Inventors: Gerhard Frisch, Wehrheim; Thomas Maier, Hofheim, both of Germany

[73] Assignee: Hoechst Schering Agreuo GmbH, Berlin, Germany

[21] Appl. No.: 571,957

[22] PCT Filed: Feb. 22, 1995

[86] PCT No.: PCT/EP95/00641

§ 371 Date: Feb. 2, 1996

§ 102(e) Date: Feb. 2, 1996

[87] PCT Pub. No.: WO95/23508

PCT Pub. Date: Sep. 8, 1995

[30] Foreign Application Priority Data

Mar. 1, 1994 [DE] Germany ............ 44 06 629.5

[51] Int. Cl.[6] ............ A01N 25/30; A01N 57/00
[52] U.S. Cl. ............ 504/116; 514/143; 514/975
[58] Field of Search ............ 514/975, 143; 504/116

[56] References Cited

U.S. PATENT DOCUMENTS

| 4,594,096 | 6/1986 | Albrecht et al. |
|---|---|---|
| 4,770,694 | 9/1988 | Iwasaki et al. ............ 514/143 |
| 4,804,399 | 2/1989 | Albrecht et al. ............ 514/975 |
| 5,547,918 | 8/1996 | Newton et al. ............ 504/116 |

FOREIGN PATENT DOCUMENTS

| 1282608 | 4/1991 | Canada . |
|---|---|---|
| 0110174 | 6/1984 | European Pat. Off. . |
| 3210869 | 10/1982 | Germany . |
| 3302648 | 8/1984 | Germany . |

*Primary Examiner*—José G. Dees
*Assistant Examiner*—Barbara Badio
*Attorney, Agent, or Firm*—Frommer Lawrence Haug LLP

[57] ABSTRACT

The present invention relates to liquid formulations of endosulfan in the form of suspension concentrates which comprise a surfactant combination of a phosphoric ester based on an ethoxylated alkylphenol and an ethoxylated alkylaryl- and alcohol phosphate ester, to processes for their preparation, and to their use in crop protection.

12 Claims, No Drawings

AQUEOUS SUSPENSION CONCENTRATES OF ENDOSULFAN

This application is a 371 of PCT/EP95/00641 filed Feb. 22, 1995.

The present invention relates to liquid formulations of endosulfan in the form of suspension concentrates.

It is known that endosulfan [1,4,5,6,7,7-hexachloro-8,9,10-trinorborn-5-en-2,3-ylenebismethylene sulfite] is an active substance having an insecticidal activity (see U.S. Pat. No. 2,799,685). The active substance may be formulated in various ways, for example as an emulsifiable concentrate (EC), wettable powder (WP), water-dispersible granules (WG), concentrated aqueous emulsion (EW) and, finally, also as a suspension concentrate (SC). The advantages of SC formulations are, mainly, no development of dust and the absence of flammable solvents, and this latter fact can have positive effects mainly on the dermal toxicity to the user.

U.S. Pat. 4,804,399 discloses an SC formulation of endosulfan which, in addition to the active substance, comprises the alkali metal salt of a sulfosuccinic monoester and an alkali metal salt of a lignosulfonic acid in a mixture with a swellable alkaline earth metal silicate. This SC formulation is relatively viscous (>400 mPas). Moreover, it comprises auxiliaries which do not meet the Environmental Protection Agency (EPA) requirements for auxiliaries (Exempt from tolerance under EPA Regulation 40 CFR 180.1001, c, d).

It must therefore be considered as surprising that it was possible to find a surfactant combination of auxiliaries which conform with EPA requirements, resulting in a stable SC formulation of endosulfan of particularly low viscosity. Moreover, these aqueous SC formulations cover a wide range of concentrations of suspended active substance, which is even more surprising, bearing in mind the high specific gravity of endosulfan (1.8 g/cm$^3$), which is markedly higher than in the case of similar active substances for SC formulations, such as isoproturon (1.2 g/cm$^3$), linuron (1.5 g/cm$^3$) and carbendazim (1.5 g/cm$^3$).

The invention therefore relates to aqueous suspension concentrates of endosulfan comprising a surfactant combination of (1) a neutralized phosphoric ester based on an ethoxylated alkylphenol and (2) an ethoxylated alkylaryl- and alcohol phosphate ester, the concentration of active substance preferably being 50 to 650 g/l, in particular 300 to 500 g/l.

The combination according to the invention of the abovementioned surfactant component (1), which is commercially available as ®Emcol CS 1361 (Witco Corp.), with the abovementioned surfactant component (2) having preferably 9EO, which is commercially available as ®Soprophor PA19 (Rhône Poulenc), is of utmost importance for the grindability in the preparation of the concentrate according to the invention and for its storage stability. This surfactant mixture, in which the ratio by weight of components (1) and (2) can vary from 100:1 to 1:100, preferably 10:1 to 1:10, in particular 3:1 to 1:3, moreover clearly suppresses crystal growth, which additionally contributes to the stability of this SC formulation over storage times of ≧3 months at temperatures of from −10° C. to +50° C.

The surfactant combination content is preferably 1 to 30% by weight, in particular 2 to 15% by weight.

Further additives or auxiliaries, preferably selected from the group of the antifoams, antifreeze agents, alkaline earth metal silicates, thickeners, preservatives, wetting agents and dispersants, may be added to the SC formulation according to the invention.

The SC formulation preferably additionally comprises 0.2 to 3% by weight of antifoam, 0 to 12% by weight of antifreeze agent, 0.5 to 10% by weight of alkaline earth metal silicate, 0 to 0.2% by weight of thickener, 0 to 2% by weight of preservative and 0 to 3% by weight of customary wetting agents and dispersants.

Examples of customary wetting agents and dispersants are polyethoxylated alkylphenols, polyethoxylated fatty alcohols, tridecyl alcohol polyglycol ether (®Genapol X-080), alkyl- or alkylphenylsulfonates, sodium lignosulfonate, sodium 2,2'-dinaphthylmethane-6,6'-disulfonate, sodium dibutylnaphthalenesulfonate or sodium oleylmethyltauride.

Examples of suitable swelling agents are swellable alumosilicates or swellable polysaccharides, such as those which are prepared by fermentation of carbohydrates by means of Xanthomonas microorganisms, such as ®Kelzan.

Other formulation auxiliaries which may be added are antifoams based on tributyl phosphate or based on silicone, such as dialkylpolysiloxanes, and antifreeze agents such as ethylene glycol, propylene glycol, glycerol, in particular propylene glycol, safeners such as, for example, urea, and customary preservatives such as, inter alia, benzoic acid, sorbic acid, formaldehyde, and traces of fungicidal active substances.

The invention also relates to a process for the preparation of the suspension concentrate according to the invention, which comprises stirring the active substance in an aqueous solution or suspension of the formulation auxiliaries and subsequently comminuting the resulting coarse suspension by grinding, if appropriate by grinding in a corundum mill or toothed-disk mill to finenesses of approximately 200 microns, and subsequently in ball mills or sand mills until the particle sizes in the suspension are 0.1 to 10 microns, preferably below 5 microns. The particle sizes can be determined by means of a disk centrifuge or a Coulter counter apparatus.

The viscosity values of the SC formulations according to the invention are 40–60 mPas at speed 15 and 60–100 mPas at speed 1. In comparison, those of the SC formulations disclosed in U.S. Pat. No. 4,804,399 are 130–180 mPas at speed 15 and 610–660 mPas at speed 1 (all these values were determined at 20° C. using a ®Rheomat 115 rotary viscometer by Contraves). Due to the low viscosity, the spontaneity of these SC formulations when diluted with water is outstanding.

The invention also relates to a method of controlling harmful insects, which comprises applying an effective amount of the abovementioned SC concentrate in the form of an aqueous dilution to these harmful insects or to the plants and soils infested with them, and to the use of the SC concentrate in crop protection.

The compositions according to the invention are simply applied by diluting the suspension concentrates with the desired amount of water, stirring the mixture briefly and applying to the plant. The spray mixtures obtained from the suspension concentrates according to the invention are distinguished from the spray mixtures prepared with wettable powders or emulsifiable concentrates in particular by the uniform distribution of the active substance, which is retained even after standing for 24 hours.

The present invention is illustrated by the examples which follow, which are compiled in Table I, without limiting the invention thereto. Table II lists examples in which a component of the surfactant mixture according to the invention was replaced and which are not storage-stable.

TABLE I

| (Percentages are by weight) | | | | | | | | | | |
|---|---|---|---|---|---|---|---|---|---|---|
| | 1 | 2 | 3 | 4 | 5 | 6 | 7 | 8 | 9 | 10 |
| Endosulfan | 39.1 | 34.44 | 30.75 | 39.1 | 39.1 | 39.1 | 35.0 | 30.8 | 25.6 | 43.5 |
| ® Emcol CS 1361 | 4.0 | 3.36 | 3.00 | 4.0 | 4.0 | 4.0 | 3.6 | 3.5 | 3.0 | 5.0 |
| ® Soprophor PA-19 | 2.0 | 1.68 | 1.50 | 2.0 | 2.0 | 2.0 | 1.8 | 1.75 | 1.5 | 2.5 |
| ® Darvan No. 3 | 1.0 | 0.84 | 0.75 | 1.0 | 1.0 | 1.0 | 1.0 | 1.0 | 1.0 | 1.0 |
| ® Hostapon T | 0.5 | 0.42 | 0.38 | 0.5 | 0.5 | 0.5 | 0.5 | 0.5 | 0.5 | 0.5 |
| ® Attapulgite Select 615 | 2.0 | 3.68 | 3.50 | — | 3.0 | 5.0 | 2.0 | 2.5 | 4.0 | 3.0 |
| ® Rhodorsil 5020 | 2.0 | 1.68 | 1.50 | 2.0 | 2.0 | 2.0 | 2.0 | 2.0 | 2.0 | 2.0 |
| ® Propylenglykol | 8.0 | 6.72 | 6.00 | 8.0 | 8.0 | 7.0 | 8.0 | 8.0 | 10.0 | 9.0 |
| ® Rhodopol 23 | — | — | — | 0.1 | — | — | — | — | — | — |
| Preservative | — | — | — | 0.1 | — | — | — | — | — | — |
| Water to 100% | | | | | | | | | | |

® Hostapon T (Hoechst AG) = sodium oleyl-N-methyltauride
® Attapulgite Select 615 (Oil Dri Corp. USA) = aluminum magnesium silicate equipped with hydrophobic properties
® Rhodorsil 5020 (Rhone Poulenc) = polydimethylsiloxane
® Darvan No. 3 (Vanderbilt Corp. USA) = sodium salt of a polymerized substituted alkylarylsulfonic acid with an inert inorganic suspending agent.

TABLE II

| (percentages are by weight) | | | | | | | |
|---|---|---|---|---|---|---|---|
| | 1 | 2 | 3 | 4 | 5 | 6 | 7 |
| Endosulfan | 39.1 | 39.1 | 39.1 | 39.1 | 39.1 | 39.1 | 39.1 |
| ® Emcol CS 1361 | 4.0 | 4.0 | 4.0 | 4.0 | 4.0 | 4.0 | 2.0 |
| ® Nekal BX | — | 2.0 | 2.0 | — | — | — | — |
| ® Arkopal N 100 | — | — | — | 2.0 | — | — | — |
| ® Soprophor 860 P | — | — | — | — | 2.0 | — | — |
| ® Witco ECD 1742 | — | — | — | — | — | 2.0 | — |
| ® Darvan No. 3 | 1.0 | 1.0 | 1.0 | 1.0 | 1.0 | 1.0 | 1.0 |
| ® Hostapon T | 0.5 | 0.5 | 0.5 | 0.5 | 0.5 | 0.5 | 0.5 |
| ® Rhodorsil 5020 | 2.0 | 2.0 | 2.0 | 2.0 | 2.0 | 2.0 | 2.0 |
| ® Attapulgite Select 615 | 2.0 | 2.0 | — | 2.0 | 2.0 | 2.0 | — |
| ® Bentone EW | — | — | 0.5 | — | — | — | — |
| ® Rhodopol 23 | — | — | — | — | — | — | 0.2 |
| Propylene glycol | 8 | 8 | 8 | 8 | 8 | 8 | 8 |
| Water to 100% | | | | | | | |

For the trademarks which are not described here in detail, see: McCutcheon's Emulsifiers & Detergents, Vol. 1, International Edition

We claim:

1. An aqueous suspension concentrate of endosulfan, comprising a surfactant combination of a neutralized phosphoric ester based on an ethoxylated alkylphenol and an ethoxylated alkylaryl- and alcohol phosphate ester.

2. A concentrate as claimed in claim 1 comprising 50 to 650 g of endosulfan/l.

3. A concentrate as claimed in claim 1, in which the ratio by weight of the two components of the surfactant combination defined in claim 1 is 100:1 to 1:100.

4. A concentrate as claimed in claim 1 comprising 1 to 30% by weight of the surfactant combination.

5. A concentrate as claimed in claim 1 comprising 2 to 15% by weight of the surfactant combination.

6. A concentrate as claimed in claim 1 comprising further additives or auxiliaries selected from the group of the antifoams, antifreeze agents, alkaline earth metal silicates, thickeners, preservatives, wetting agents and dispersants.

7. A concentrate as claimed in claim 1 additionally comprising 0.2 to 3% by weight of antifoam, 0 to 12% by weight of antifreeze agent, 0.5 to 10% by weight of alkaline earth metal silicate, 0 to 0.2% by weight of thickener, 0 to 2% by weight of preservative and 0 to 3% by weight of customary wetting agent and dispersant.

8. A process for the preparation of a concentrate as claimed in claim 1, which comprises stirring the active substance in an aqueous solution or suspension of the formulation auxiliaries and subsequently comminuting the resulting coarse suspension by grinding.

9. A method of controlling harmful insects, which comprises applying an effective amount of a concentrate as claimed in claim 1 in the form of an aqueous dilution to these harmful insects or to the plants and soils infested with them.

10. A crop protectant comprising a concentrate as claimed in claim 1.

11. An aqueous suspension concentration of endosulfan consisting essentially of a surfactant combination consisting essentially of neutralized phosphoric ester based on an ethoxylated alkylphenol and an ethoxylated alkylaryl- and alcohol phosphate ester.

12. A method of controlling harmful insects comprising applying an aqueous dilution of the concentrate of claim 11 to the insects, or plants or soil infested with the insects.

* * * * *